(12) United States Patent
Christensen

(10) Patent No.: US 6,911,052 B2
(45) Date of Patent: Jun. 28, 2005

(54) PROSTHETIC FOOT WITH OBLIQUE ATTACHMENT

(75) Inventor: Roland J. Christensen, Fayette, UT (US)

(73) Assignee: Roland J. Christensen, as operating Manager of RJC Development, LC, General Partner of the Roland J. Christensen Family Limited Partnership, Fayette, UT (US)

( * ) Notice: Subject to any disclaimer, the term of this patent is extended or adjusted under 35 U.S.C. 154(b) by 0 days.

(21) Appl. No.: 10/268,013

(22) Filed: Oct. 8, 2002

(65) Prior Publication Data

US 2004/0068326 A1 Apr. 8, 2004

(51) Int. Cl.$^7$ .................................................. A61F 2/66
(52) U.S. Cl. .................................................. 623/52
(58) Field of Search ............................ 623/52, 53, 54, 623/55, 56, 35, 38, 46, 49, 50

(56) References Cited

U.S. PATENT DOCUMENTS

| | | | |
|---|---|---|---|
| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,191,633 A | 5/1916 | Waggott |
| 1,779,765 A | 10/1930 | Eichhorn |
| 1,996,874 A | 4/1935 | Mascau |
| 2,036,830 A | 4/1936 | Rowley |
| 2,379,538 A | 7/1945 | Meierhofer |
| 2,443,356 A | 6/1948 | Mathis |
| 2,453,969 A | 11/1948 | Carter |
| 2,470,480 A | 5/1949 | Fogg |
| 2,570,735 A | 10/1951 | Weise |
| 2,617,115 A | 11/1952 | Ellery |
| 2,640,200 A | 6/1953 | Wisbrun |
| 2,843,853 A | 6/1958 | Mauch |
| 3,551,914 A | 1/1971 | Woodall |
| 3,871,032 A | 3/1975 | Karas |
| 3,906,552 A | 9/1975 | Weber |
| 3,920,610 A | 11/1975 | Wagner |
| 3,956,775 A | 5/1976 | Moore |
| 3,982,280 A | 9/1976 | Asbelle et al. |
| 4,089,072 A | 5/1978 | Glabiszewski |
| 4,328,594 A | 5/1982 | Campbell et al. |
| 4,506,395 A | 3/1985 | Haupt |
| 4,547,913 A | 10/1985 | Phillips |
| 4,645,509 A | 2/1987 | Poggi et al. |
| 4,676,801 A | 6/1987 | Lundeen |
| 4,721,510 A | 1/1988 | Cooper et al. |
| 4,822,363 A | 4/1989 | Phillips |
| 4,865,611 A | 9/1989 | Al-Turaiki |
| 4,938,775 A | 7/1990 | Morgan |

(Continued)

FOREIGN PATENT DOCUMENTS

| | | |
|---|---|---|
| DE | 295807 | 12/1916 |
| GB | 1550-658 | 8/1979 |
| IT | 556381 | 11/1958 |
| RU | 2033772 | 4/1995 |
| SU | 560606 | 7/1977 |

*Primary Examiner*—Bruce E Snow
(74) *Attorney, Agent, or Firm*—Thorpe North & Western

(57) ABSTRACT

A prosthetic foot device includes an oblique attachment. The foot device can include an elongated forefoot portion having an upper attachment section disposed at an oblique angle and attached to an oblique surface of an attachment member coupled to a limb of an amputee. The forefoot portion can extend through ankle, arch and toe sections. The ankle section can include a discrete straight section that is vertically oriented and located at a rearmost of the foot device. The attachment section can extend to a position at the first third of a length of the foot device measured from the rearmost of the foot device. The foot device can be an energy storing and releasing member during use.

14 Claims, 2 Drawing Sheets

U.S. PATENT DOCUMENTS

| | | | | |
|---|---|---|---|---|
| 4,959,073 A | | 9/1990 | Merlette | |
| 5,019,109 A | | 5/1991 | Voisin | |
| 5,030,239 A | | 7/1991 | Copes | |
| 5,037,444 A | | 8/1991 | Phillips | |
| 5,112,356 A | | 5/1992 | Harris et al. | |
| 5,116,383 A | | 5/1992 | Shorter et al. | |
| 5,116,384 A | | 5/1992 | Wilson et al. | |
| 5,181,932 A | | 1/1993 | Phillips | |
| 5,181,933 A | | 1/1993 | Phillips | |
| 5,217,500 A | | 6/1993 | Phillips | |
| 5,290,319 A | | 3/1994 | Phillips | |
| 5,376,133 A | | 12/1994 | Gramnas | |
| 5,376,141 A | | 12/1994 | Phillips | |
| 5,387,246 A | | 2/1995 | Phillips | |
| 5,425,781 A | | 6/1995 | Allard et al. | |
| 5,425,782 A | | 6/1995 | Phillips | |
| 5,443,528 A | | 8/1995 | Allen | |
| 5,443,529 A | | 8/1995 | Phillips | |
| 5,458,656 A | | 10/1995 | Phillips | |
| 5,464,441 A | | 11/1995 | Phillips | |
| 5,482,513 A | | 1/1996 | Wilson | |
| 5,486,209 A | | 1/1996 | Phillips | |
| 5,507,838 A | | 4/1996 | Chen | |
| 5,509,936 A | | 4/1996 | Rappoport et al. | |
| 5,509,937 A | * | 4/1996 | Allard et al. | 623/55 |
| 5,509,938 A | | 4/1996 | Phillips | |
| 5,514,185 A | | 5/1996 | Phillips | |
| 5,514,186 A | | 5/1996 | Phillips | |
| 5,549,714 A | | 8/1996 | Phillips | |
| 5,571,210 A | | 11/1996 | Lindh | |
| 5,571,213 A | | 11/1996 | Allen | |
| 5,593,455 A | | 1/1997 | Phillips | |
| 5,593,456 A | | 1/1997 | Merlette | |
| 5,593,457 A | | 1/1997 | Phillips | |
| 5,653,767 A | | 8/1997 | Allen et al. | |
| 5,725,598 A | | 3/1998 | Phillips | |
| 5,728,175 A | | 3/1998 | Rincoe | |
| 5,728,176 A | | 3/1998 | Phillips | |
| 5,728,177 A | | 3/1998 | Phillips | |
| 5,766,265 A | | 6/1998 | Phillips | |
| 5,769,896 A | | 6/1998 | Rosendahl et al. | |
| 5,776,205 A | | 7/1998 | Phillips | |
| 5,779,735 A | | 7/1998 | Molino | |
| 5,800,565 A | | 9/1998 | Biedermann | |
| 5,800,569 A | | 9/1998 | Phillips | |
| 5,824,112 A | | 10/1998 | Phillips | |
| 5,888,238 A | | 3/1999 | Phillips et al. | |
| 5,893,891 A | | 4/1999 | Zahedi | |
| 5,899,944 A | | 5/1999 | Phillips | |
| 5,976,191 A | | 11/1999 | Phillips | |
| 5,993,488 A | | 11/1999 | Phillips | |
| 6,019,795 A | | 2/2000 | Phillips | |
| 6,071,313 A | | 6/2000 | Phillips | |
| 6,099,572 A | * | 8/2000 | Mosler et al. | 623/53 |
| 6,165,227 A | | 12/2000 | Phillips | |
| 6,197,068 B1 | * | 3/2001 | Christensen | 623/55 |
| 6,206,934 B1 | | 3/2001 | Phillips | |
| 6,254,643 B1 | | 7/2001 | Phillips | |
| 6,261,324 B1 | | 7/2001 | Merlette | |
| 6,280,479 B1 | | 8/2001 | Phillips | |
| 6,290,730 B1 | | 9/2001 | Pitkin et al. | |
| 2003/0019540 A1 | * | 1/2003 | Townsend et al. | 623/55 |
| 2003/0045944 A1 | * | 3/2003 | Mosler et al. | 623/52 |

* cited by examiner

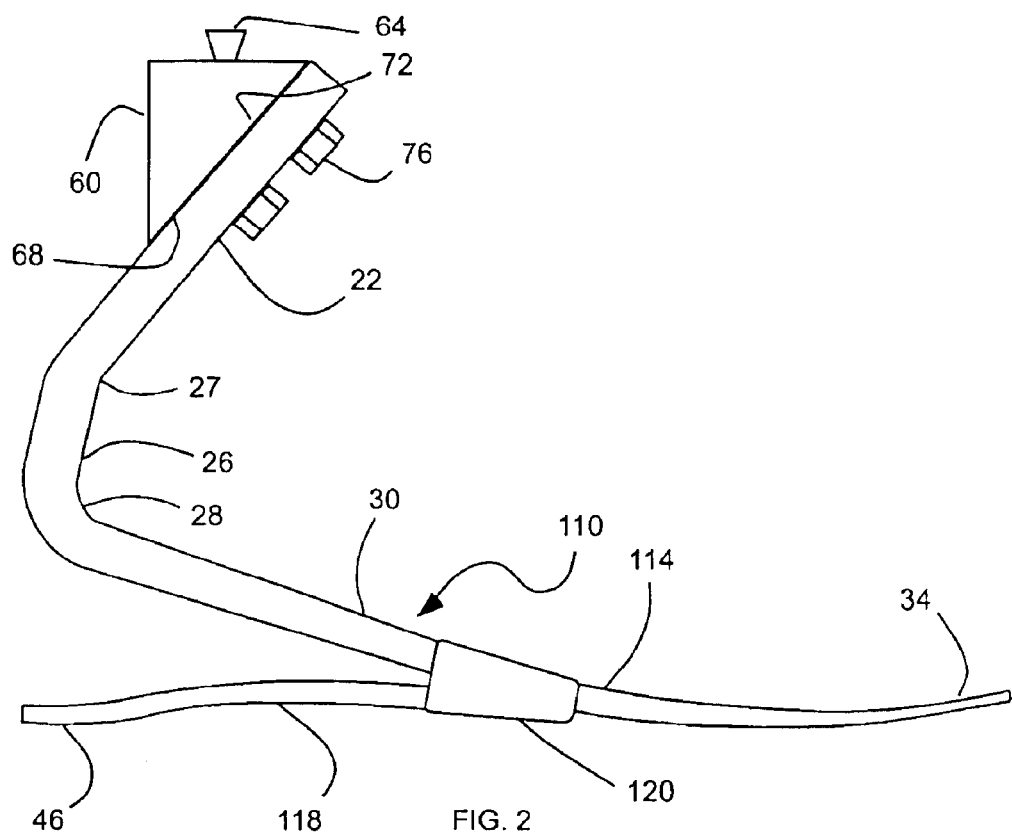
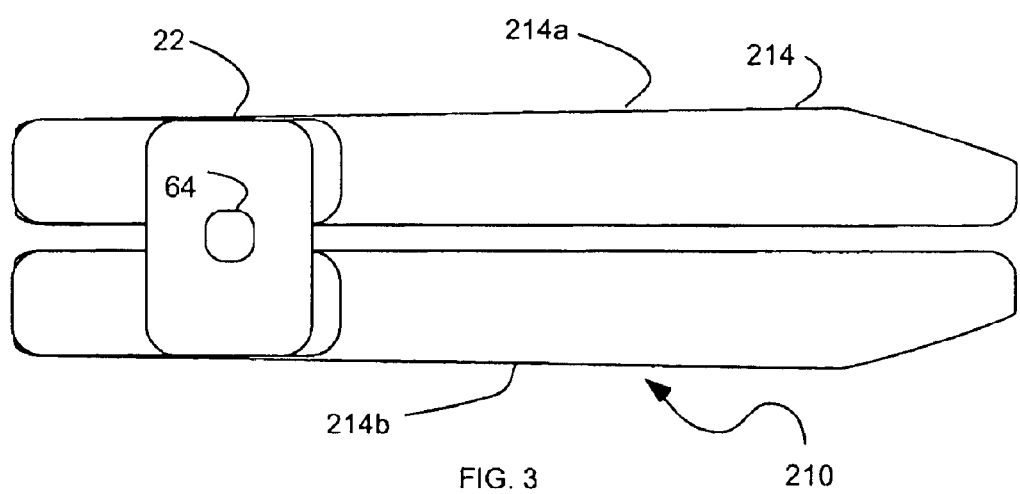

PROSTHETIC FOOT WITH OBLIQUE ATTACHMENT

BACKGROUND OF THE INVENTION

1. Field of the Invention

The present invention relates generally to prosthetic feet. More particularly, the present invention relates to prosthetic feet with an oblique attachment angle.

2. Related Art

Many individuals have lost a limb for various reasons including war, accident, or disease. In most instances these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element, such as a spring. As the user steps onto the foot, the user's weight compresses the spring. As the user moves forward, the user's weight comes off the foot and the energy stored in the spring is used to propel the user forward.

In addition, the performance of these energy storing feet has been altered in various ways, such as by using multiple springs in various configurations, using bladders or resilient materials disposed between various elements, and using multiple springs that deflect at different intervals of foot deflection to add resistance.

As described above, such energy-storing prosthetic feet typically have either a J-shape or a C-shape configuration or profile. The J-shape feet have a vertical attachment section, while the C-shaped feet have a horizontal attachment section. While the vertical attachment section of the J-shape feet can be relatively long, depending on the length of the residual limb of the amputee, the horizontal attachment section of the C-shape feet tend to be relatively short, due to the constraint of having the prosthetic foot contained in a general outline of a natural foot. It will be appreciated that the shape and dimensions of the foot can affect or limit the performance or bending characteristics of the foot.

SUMMARY OF THE INVENTION

The continued development of improved prosthetic feet is an ongoing goal. It has been recognized that it would be advantageous to develop an energy-storing foot with improved bending characteristics, and cushion and shock absorbing characteristics.

The invention provides an energy-storing, prosthetic foot with an oblique attachment. An elongated forefoot portion has an upper attachment section to be coupled to a limb of an amputee, and extends downwardly through an ankle section, forwardly through an arch section, and to a toe section. The ankle section can be positioned at an ankle location of a natural foot, while the toe section can be positioned at a toe location of a natural foot. The attachment section advantageously is disposed at an oblique angle. The oblique angle can allow the attachment section to be relatively longer than a horizontal attachment of a C-shaped foot, while retaining a relatively low elevation with respect to the vertical attachment of a J-shaped foot. The longer length of the forefoot portion allows extra length to store and return energy during use, contributes to extra spring or cushion of the foot, and improves vertical shock resistance.

In accordance with a more detailed aspect of the present invention, the foot device can include an attachment member coupled between the stump of the amputee and the attachment section of the upper forefoot portion. The attachment member can have a lower oblique surface attached to an upper oblique surface of the attachment section of the upper forefoot portion.

In accordance with another more detailed aspect of the present invention, the prosthetic foot can include a discrete, straight section oriented substantially vertically with curved sections on both sides. The discrete, straight ankle section allows extra length to store and return energy during use, contributes to extra spring or cushion of the foot, and improves vertical shock resistance.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 1b is a top view of the prosthetic foot of FIG. 1a;

FIG. 2 is a side view of a prosthetic foot in accordance with an embodiment of the present invention; and FIG. 3 is a top view of a prosthetic foot in accordance with an embodiment of the present invention.

DETAILED DESCRIPTION

Figure 1A:
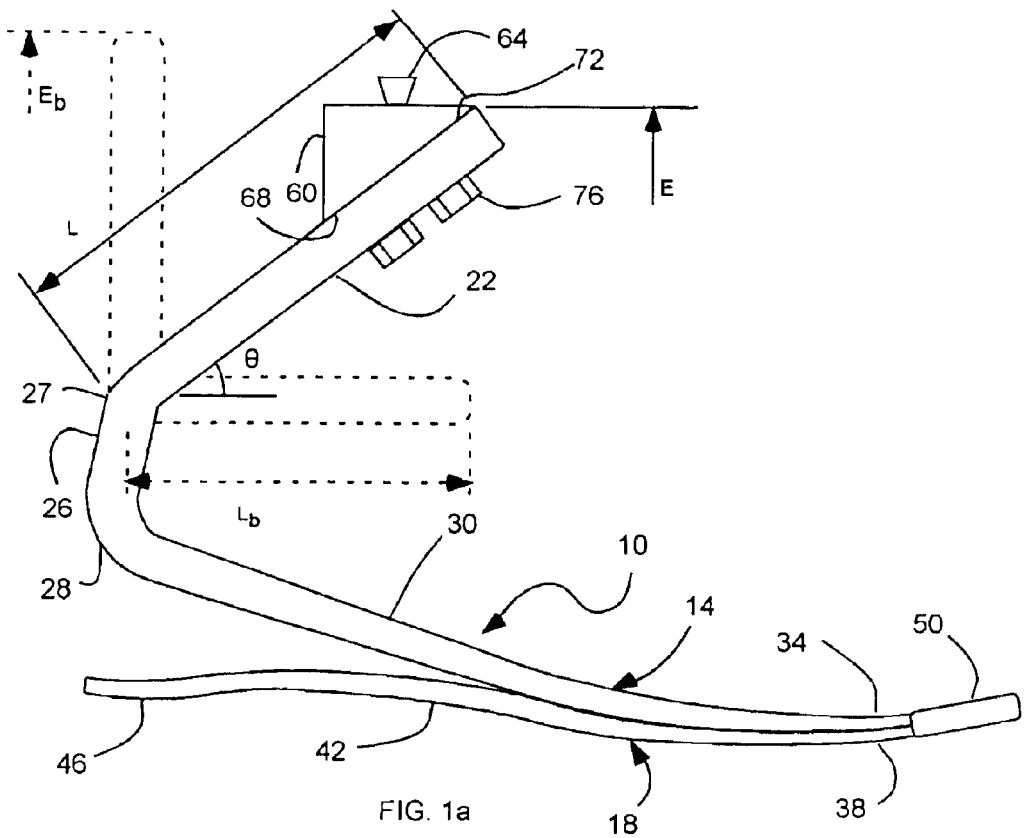
FIG. 1a is a side view of a prosthetic foot in accordance with an embodiment of the present invention.
Figure 1B:
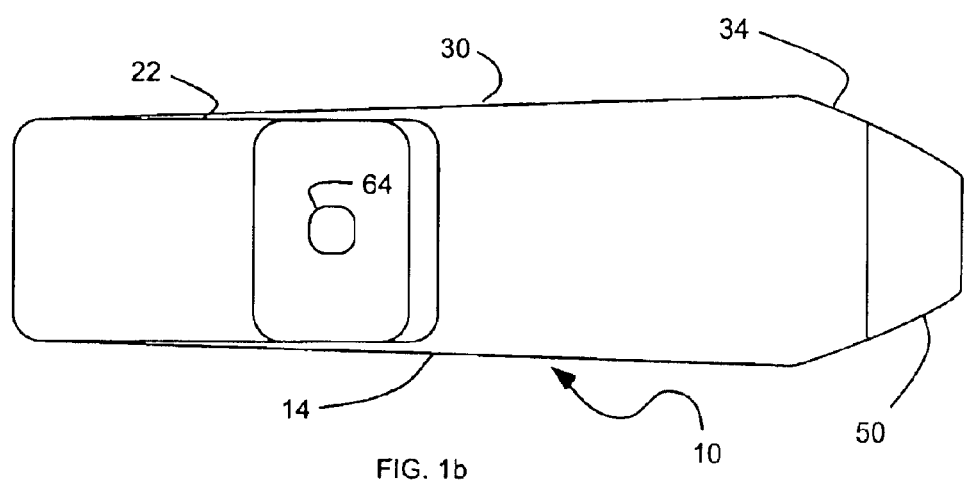

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1a and b, a prosthetic foot, indicated generally at 10, in accordance with the present invention is shown with an oblique attachment, or an attachment forming an oblique angle. The foot 10 can include an elongated, upper forefoot portion or foot member 14, and a lower footplate 18. The foot member 14 can include an upper attachment section 22 to be coupled to a limb of an amputee. As discussed below, the attachment section 22 can be oblique, or can be disposed at an oblique angle. The foot member 14 can extend downwardly and rearwardly through the attachment section 22, downwardly through an ankle section 26, forwardly through an arch section 30, and to a toe section 34. The ankle section 26 is positioned at an ankle location of a natural foot. Likewise, the toe section 34 is positioned at a toe location of a natural foot. The toe location is a region near the forward end of the foot where toes of a natural foot would be located.

The foot member 14 or ankle section 26 can be substantially arcuate. The arc formed by the ankle section can be smoothly curved, or can be formed of both straight and curved sections. The foot member 14 or ankle section 26 forms a vertically oriented arc extending between the attachment section 22 and the arch or toe sections. Thus, the foot member or ankle section can form a curvilinear spring portion.

The lower footplate 18 can be attached to the foot member 14, and disposed foot member 14. The lower footplate 18 can extend rearwardly through a toe section 38, through an arch section 42, and to a heel section 46. The toe section 38 is positioned at a toe location of a natural foot. Likewise, the heel section 46 is positioned at a heel location of a natural foot. The heel location is a region near the rearward end of the foot where the heel of a natural foot would be located. The toe section 38 of the lower footplate 18 can be attached to the toe section 34 of the foot member 14. The attachment 50 can be formed by wrapping the toe sections 34 and 38 with fibers in a resin matrix.

The foot 10 also can include an attachment member 60 to attach the foot member 14 to a socket configured for the specific needs of the amputee. Such sockets typically have a portion adapted for standard attachment. The attachment member 60 can include a pyramid connector 64 on a top end or upper surface, as is well known in the art to connect to a socket on the stump of the amputee. In addition, the attachment member 60 can include a lower oblique surface 68 that faces forwardly. The attachment section 22 of the upper foot member 14 can include an upper oblique surface 72 that faces rearwardly and matches and attaches to the lower oblique surface 68. The attachment section 22 can be coupled to the attachment member 60 by fasteners, such as bolts 76. For example, the bolts 76 can extend through apertures in the attachment section 22 of the foot member 14 and into threaded bores in the attachment member 60. It is of course understood that any type of fastener or connection can be used, including for example, screws, clips, wrap of resin impregnated fiber, etc.

As discussed above, the attachment section 22 of the foot member 14, and the upper and lower oblique surfaces 72 and 68, are oblique or oriented at an oblique angle Θ. The oblique angle is with respect to horizontal while the foot device 10 is disposed on a support surface in a substantially unloaded condition, and the oblique angle is oriented in a vertical plane that is aligned longitudinally, or fore and aft, with respect to the foot device 10, so that the attachment section 22, or oblique surface 72, extends upwardly and forwardly. In one aspect, the attachment section 22 can be oriented between approximately 20 and 70 degrees with respect to a horizontal axis. In another aspect, the attachment section 22 can be oriented between approximately 30 and 60 degrees with respect to a horizontal axis. In another aspect, the attachment section 22 can be oriented at approximately 45 degrees with respect to a horizontal axis, as shown. The attachment section 22 can extend upwardly and forwardly from the ankle section 26. Thus, the foot member 14 extends rearwardly and downwardly through the attachment section 22, downwardly through the ankle section 26, and forwardly and downwardly through the arch and toe sections 30 and 34.

The oblique angle of the attachment section 22 allows the attachment section 22 to extend a horizontal distance $L_b$ while having a longer length L. It will be appreciated that a horizontal attachment section, as shown in dashed lines, has a length $L_b$ that is relatively short compared to the length L of the attachment section 22. In addition, the oblique angle of the attachment section 22 allows the attachment section 22 to have a longer length L while extending to vertical elevation E. It will be appreciated that a vertical attachment section, as shown in dashed lines, with the same length extends to a relatively higher vertical elevation $E_b$ than the relatively lower vertical elevation E of the attachment section 22. Thus, the attachment section 22 can provide a longer lever arm while having a shorter vertical elevation. Thus, the attachment section 22 of the present invention extending at an oblique angle allows a longer length L without extending beyond a vertical elevation of a vertical attachment section of a J-shape. The longer length of the attachment section 22 allows extra length to store and return energy during use, contributes to extra spring or cushion of the foot, and improves vertical shock resistance.

In addition, the pyramid connector 64 can be moved fore or aft, or forward or rearward, to change the bending characteristics of the foot member 14 or foot 10. In one aspect, the pyramid connector 64, or other connector, can be positioned at approximately the first third of the foot 10, with respect to, or measured from, the rearmost of the foot, as shown in FIGS. 1a and b. Alternatively the connector can be positioned at approximately the first quarter, as shown in FIGS 2 and 3. Positioning the connector at the first third provides a longer lever arm to store and return energy during use, contributes to extra spring or cushion of the foot, and improves vertical shock resistance.

The entire foot 10, or the foot member 14 and lower footplate 18, can be an energy-storing member that flexes and bends under a load to store energy, and returns to its original configuration while the load is released to release the stored energy. The foot member 14 and footplate 18 can include or be formed of a flexible and resilient material. For example, the material can be a composite with fibers disposed in a resin matrix. The fiber can be disposed in unidirectional, mat or weave with several layers. As the amputee steps, or pivots forward, on the prosthetic foot 10, the foot member 14 deflects. Because the foot member 14 is made of a resilient material, the foot member 14 acts as a spring, and stores the energy to be released as the user moves forward. Similarly, as the user steps on the footplate 18, the footplate deflects and stores energy to be released as the amputee pivots forward.

Referring to FIG. 2, another prosthetic foot 110 is shown that is similar in many respects to the foot described above. The foot 110 can include a foot member 114, similar to that above, and a heel portion 118. The heel portion 118 can have an attachment section 120 attached to the arch section 30 of the foot member 114, and extending rearwardly to a heel section 46 positioned at a heel location of a natural foot. The attachment can be formed by wrapping the attachment section 120 of the heel portion 118 and the arch section 30 of the foot member 114 with fibers in a resin matrix. As above, the foot member and heel portions 114 and 118 can be energy-storing members.

Referring to FIG. 3, another prosthetic foot 210 is shown that can be similar in many respects to those described above. The foot 210 can include a foot member 214, similar to those described above. The foot also can include either a lower footplate or a lower heel portion, similar to those described above. The foot member 214 can include two or more portions, such as first and second portions 214a and b, disposed adjacent one another in a side-by-side relationship. The two portions 214a and b can be laterally separated by a gap. The two portions allow the foot member to mimic the toe rotation of a natural foot. The first and second portions 214a and b can be independently movable with respect to one another. Because the foot 10 includes the two portions, the foot 10 is able to respond to uneven terrain more like a natural foot with rotating toes. In addition, the foot 10 is better able to simulate toe and axial foot rotation. The foot member can be split along substantially the entire length. The footplate or heel portion can be similarly split. It is of course understood that the foot member, footplate, and/or heel portion can be partially or wholly split. The first and second portions can be mirror images of one another, or can be configured to resemble an actual foot. In addition, the first and second portions can have different spring forces, or stiffness, to better simulate a natural foot.

Referring again to FIGS. 1a and 2, the ankle section 26 of the foot member 14 or 114 can include a discrete, straight section that is oriented substantially vertically. A first curved section 27 can interconnect the attachment section 22 and the ankle section 26. Similarly, a second curved section 18 can interconnect the ankle section 26 and the arch section 30. Thus, the ankle section 26 can include the discrete, straight section intermediate two curved sections 27 and 28. The foot member 14 or 114 thus can extend 1) rearwardly and/or downwardly through the attachment section 22, 2) rearwadly and downwardly through the first curved section 27, 3) downwardly through the straight section or ankle section 26, 4) downwardly and forwardly through the second curved section 28, 5) forwardly and/or downwardly through the arch section 30, and 6) to the toe section 34. The discrete straight section of the ankle section 26 allows the foot member 14 to be longer, and thus to store and return more energy during use, contributes to extra spring or cushion of the foot, and improves vertical shock resistance.

In addition, the ankle section 26 of the foot member 14 or 114 can be positioned at a rearmost location of the foot device 10 or 110, and over the heel section 46 of the lower footplate 18 or heel portion 118. Thus, the foot member 14 extends from the toe section 34 at the front of the foot, to above the heel section 46 at the rear of the foot. Thus, the foot member 14 or 114 can be further elongated to store and return energy during use, to contribute to extra spring or cushion of the foot, and to improve vertical shock resistance.

The prosthetic feet disclosed above can be provided with the foot member alone, without a lower footplate or heel portion.

Various aspects of such energy-storing prosthetic feet are shown and described in U.S. Pat. Nos. 5,944,760; 6,197,068; and 6,241,776, which are herein incorporated by reference.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. A prosthetic foot device, comprising:
   a) an attachment member, configured to be coupled to a limb of an amputee, having a lower oblique surface facing forwardly;
   b) an elongated foot member having 1) an upper attachment section, attached to the oblique surface of the attachment member, and disposed at an oblique angle with respect to horizontal between 30 and 60 degrees when the foot device is in an unloaded condition on a support surface, and the oblique angle being disposed in a vertical plane aligned longitudinally with the foot member, 2) an ankle section extending downwardly from the attachment section, 3) an arch section extending from the ankle section, and 4) a toe section extending from the arch section and positioned at a toe location of a natural foot; and
   c) a lower footplate, attached to the foot member, having a toe section positioned at a toe location of a natural foot, extending through an arch section to a heel section positioned at a heel location of a natural foot.

2. A device in accordance with claim 1, wherein the foot member is flexible to store energy and resilient to return energy.

3. A device in accordance with claim 2, wherein the foot member includes a composite material with fiber in a resin matrix.

4. A device in accordance with claim 1, wherein the toe section of the lower footplate is attached to the toe section of the foot member.

5. A device in accordance with claim 1, further comprising:
   an elongated heel portion, attached to the foot member, having an attachment section attached to the foot member, and extending to a heel section positioned at a heel location of a natural foot.

6. A device in accordance with claim 1, wherein the foot member includes at least two laterally separated and adjacent foot members.

7. A device in accordance with claim 1, wherein the attachment section of the foot member extends to a position approximately at the first third of a length of the foot device from a rearmost of the foot device; and wherein the ankle section of the foot member is positioned at the rearmost of the foot device.

8. A prosthetic foot device, comprising:
   a) an attachment member, configured to be coupled to a limb of an amputee, having a lower oblique surface facing forwardly;
   b) an elongated, foot member, attached to the attachment member, extending through 1) an upper oblique attachment section with an upper oblique attachment surface facing rearwardly and attached to the lower oblique surface of the attachment member, the oblique attachment section being disposed at an oblique angle with respect to horizontal between 30 and 60 degrees when the foot device is in an unloaded condition on a support surface, and the oblique angle being disposed in a vertical plane aligned longitudinally with the foot member, 2) an ankle section positioned at an ankle location of a natural foot, 3) an arch section, to 4) a toe section positioned at a toe location of a natural foot; and
   c) a lower footplate, attached to the foot member, having a toe section positioned at a toe location of a natural foot, extending through an arch section to a heel section positioned at a heel location of a natural foot; and
   d) the foot member and the lower footplate each being formed of a flexible and resilient material to form energy storing flexing members.

9. A device in accordance with claim 8, wherein the foot member includes a composite material with fiber in a resin matrix.

10. A device in accordance with claim 8, wherein the toe section of the lower footplate is attached to the toe section of the foot member.

11. A device in accordance with claim 8, wherein the foot member and lower footplate each include at least two laterally separated and adjacent portions.

12. A device in accordance with claim 8, wherein the attachment section of the foot member extends to a position approximately at the first third of a length of the foot device from a rearmost of the foot device; and wherein the ankle section of the foot member is positioned at the rearmost of the foot device.

13. A device in accordance with claim 1, wherein the attachment section of the foot member extends forwardly and upwardly from the ankle section.

14. A device in accordance with claim 8, wherein the attachment section of the foot member extends forwardly and upwardly from the ankle section.

* * * * *